United States Patent
Kobayashi et al.

(10) Patent No.: US 12,394,118 B2
(45) Date of Patent: Aug. 19, 2025

(54) LIST MODE IMAGE RECONSTRUCTION METHOD AND NUCLEAR MEDICINE DIAGNOSTIC APPARATUS

(71) Applicant: Shimadzu Corporation, Kyoto (JP)

(72) Inventors: Tetsuya Kobayashi, Kyoto (JP); Yoshihiro Yamada, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 373 days.

(21) Appl. No.: 17/910,468

(22) PCT Filed: Mar. 16, 2020

(86) PCT No.: PCT/JP2020/011486
§ 371 (c)(1),
(2) Date: Sep. 9, 2022

(87) PCT Pub. No.: WO2021/186504
PCT Pub. Date: Sep. 23, 2021

(65) Prior Publication Data
US 2023/0056540 A1  Feb. 23, 2023

(51) Int. Cl.
*G06T 11/00* (2006.01)
*G01T 1/161* (2006.01)

(52) U.S. Cl.
CPC ........... *G06T 11/006* (2013.01); *G01T 1/161* (2013.01); *G06T 2211/424* (2013.01)

(58) Field of Classification Search
CPC .... G06T 11/006; G06T 221/424; G01T 1/161
See application file for complete search history.

(56) References Cited

U.S. PATENT DOCUMENTS

| | | | |
|---|---|---|---|
| 2017/0249735 A1* | 8/2017 | Feng | G06T 7/0012 |
| 2020/0249369 A1* | 8/2020 | Qiang | G01T 7/005 |
| 2021/0104079 A1* | 4/2021 | Whiteley | G06N 3/084 |

FOREIGN PATENT DOCUMENTS

| | | | | |
|---|---|---|---|---|
| CN | 108257108 | * | 6/2018 | G06T 5/50 |

OTHER PUBLICATIONS

Bailey et al., "A convolution-subtraction scatter correction method for 3D Pet", Phys. Med. Biol. 39 (1994) pp. 411-424.
Burger et al., "PET attenuation coefficients from CT images: experimental evaluation of the transformation of CT into PET 511-keV attenuation coefficients", European Journal of Nuclear Medicine vol. 29, No. 7, Apr. 19, 2002.
Nakayama et al., "Derivation and Implementation of Ordered-Subsets Algorithms for List-Mode PET Data", 2005 IEEE Nuclear Science Symposium Conference Record, 2005, pp. 1950-1954.
Popescu et al., "Iterative image reconstruction using geometrically ordered subsets with list-mode data," Paper presented at Nuclear Science Symp. Medical Imaging Conf., 2004, Rome.
(Continued)

*Primary Examiner* — Myron Wyche
(74) *Attorney, Agent, or Firm* — Muir Patent Law, PLLC

(57) ABSTRACT

A list mode image reconstruction method includes a step of dividing list mode data into a plurality of subsets and a step of acquiring a subset balance coefficient based on the number of events in the plurality of subsets.

11 Claims, 6 Drawing Sheets

(56) References Cited

OTHER PUBLICATIONS

Rahmim et al., "Statistical List-mode Reconstruction in Quantitative Dynamic Imaging using the High Resolution Research Tomograph," Fully 3D Reconstr. Meeting in Radiol. and Nucl. Med., Salt Lake City, Utah, 2005.

Reader et al., "Fast accurate iterative reconstruction for low-statistics positron volume imaging", Phys. Med. Biol. 43 (1998) pp. 835-846.

Rezaei et al., "ML-Reconstruction for TOF-PET With Simultaneous Estimation of the Attenuation Factors", IEEE Transactions on Medical Imaging, vol. 33, No. 7, Jul. 2014, pp. 1563-1572.

Rezaei et al., "Simultaneous Reconstruction of Activity and Attenuation in Time-of-Flight Pet", IEEE Transactions on Medical Imaging, vol. 31, No. 12, Dec. 2012, pp. 2224-2233.

Wang et al., "Systematic and Distributed Time-of-Flight List Mode PET Reconstruction", 2006 IEEE Nuclear Science Symposium Conference Record, 2006, pp. 1715-1722.

Written Opinion for PCT application No. PCT/JP2020/011486, dated Jun. 16, 2020, submitted with a machine translation.

\* cited by examiner

Measurement time (reconstruction time range) Tacq

Concept of subset balance coefficient

LIST MODE IMAGE RECONSTRUCTION METHOD AND NUCLEAR MEDICINE DIAGNOSTIC APPARATUS

TECHNICAL FIELD

The present invention relates to a list mode image reconstruction method and a nuclear medicine diagnostic apparatus.

BACKGROUND ART

Conventionally, a list mode image reconstruction method is known in which a radioactivity distribution of a subject is reconstructed by iterative calculation from list mode data collected by a nuclear medicine diagnostic apparatus. Such a list mode image reconstruction method is disclosed in, for example, Wang, W., et al. "Systematic and distributed time-of-flight list mode PET reconstruction." 2006 IEEE Nuclear Science Symposium Conference Record. Vol. 3. IEEE, 2006 (hereinafter simply referred to as "Non-Patent Document 1").

In Non-Patent Document 1, a list mode image reconstruction method is disclosed in which a radioactivity distribution of a subject is reconstructed from list mode data collected by a PET device (nuclear medicine diagnostic apparatus) by iterative calculation.

PRIOR ART DOCUMENT

Patent Document

Non-Patent Document 1: Wang, W., et al. "Systematic and distributed time-of-flight list mode PET reconstruction," 2006 IEEE Nuclear Science Symposium Conference Record. Vol. 3. IEEE, 2006

SUMMARY OF THE INVENTION

Problems to be Solved by the Invention

However, in a conventional list mode image reconstruction method as described in the above-described Non-Patent Document 1, there are the following drawbacks. That is, in a case where the number of events between subsets obtained by dividing list mode data is uneven, the calculated value of iterative calculation may not converge to a value indicating a radioactive concentration of a subject due to the uneven number of events between subsets. In this case, there is a drawback that a quantitative radioactivity distribution image cannot be generated. Further, in a case where the number of subsets is changed, there is a drawback that the pixel value changes depending on the subset. For these reasons, a conventional list mode image reconstruction method has a drawback that it is difficult to generate a quantitative radioactivity distribution image without depending on the number of subsets.

The present invention has been made to solve the above-described problems. It is an object of the present invention to provide a list mode image reconstruction method and a nuclear medicine diagnostic apparatus capable of generating a quantitative radioactivity distribution image without depending on the number of subsets.

Means for Solving the Problem

In order to achieve the above-described object, a list mode image reconstruction method according to a first aspect of the present invention is a list mode image reconstruction method for reconstructing a radioactivity distribution of a subject from list mode data collected by a nuclear medicine diagnostic apparatus by iterative calculation, the list mode image reconstruction method comprising the steps of:
 dividing the list mode data into a plurality of subsets;
 acquiring subset balance coefficients based on the number of events in the plurality of subsets;
 acquiring back projection values based on the list mode data;
 acquiring a back projection image based on the back projection values;
 multiplying the back projection values or the back projection image by the subset balance coefficient; and
 updating a radioactivity distribution image based on the back projection image.

Note that the terminology "list mode data" means data in which radiation detection event information (a detector number, a detection time, energy of radiation, and the like) is stored in time series.

Further, a nuclear medicine diagnostic apparatus according to a second aspect of the present invention, includes:
 a detection unit configured to detect radiation generated from a radiopharmaceutical agent in a subject; and
 an operation unit configured to reconstruct a radioactivity distribution of the subject from list data as a detection result of radiation by the detection unit by iterative calculation,
 wherein the operation unit
 divides the list mode data into a plurality of subsets,
 acquires subset balance coefficients based on the number of events in the plurality of subsets,
 acquires back projection values based on the list mode data,
 acquires a back projection image based on the back projection values,
 multiplies the back projection values or the back projection image by the subset balance coefficient, and
 updates a radioactivity distribution image based on the back projection image.

Effects of the Invention

According to the present invention, as described above, list mode data is divided into a plurality of subsets, subset balance coefficients are acquired based on the number of events in the plurality of subsets, back projection values are acquired based on the list mode data, a back projection image is acquired based on the back projection values, back projection values or a back projection image is multiplied by subset balance coefficients, and a radioactivity distribution image is updated based on the back projection image. With this configuration, by introducing the subset balance coefficient, it is possible to adjust the unevenness of the number of events between subsets. Therefore, it is possible to suppress that the calculated value (pixel value) of the iterative calculation does not converge to the value indicating the radioactive concentration of the subject due to the unevenness of the number of events between subsets. In other words, it is possible to make the calculated value of the iterative calculation converge to a value indicating the radioactive concentration of a subject, and therefore, a quantitative radioactivity distribution image can be generated. Further, even in a case where the number of subsets is changed by introducing the subset balance coefficient, the unevenness of the number of events between subsets can be adjusted, and therefore, it is possible to suppress the change in the pixel value depending on the number of subsets. In other words, an equivalent pixel value can be acquired without depending on the number of subsets. As a result, a quantitative radioactivity distribution image can be generated without depending on the number of subsets.

EMBODIMENTS FOR CARRYING OUT THE INVENTION

Hereinafter, some embodiments in which the present invention is embodied will be described with reference to the attached drawings.
Configuration of PET Device With reference to FIG. 1 and FIG. 2, a configuration of a PET (Positron Emission Tomography) device 1 according to a first embodiment will be described.

Figure 1:
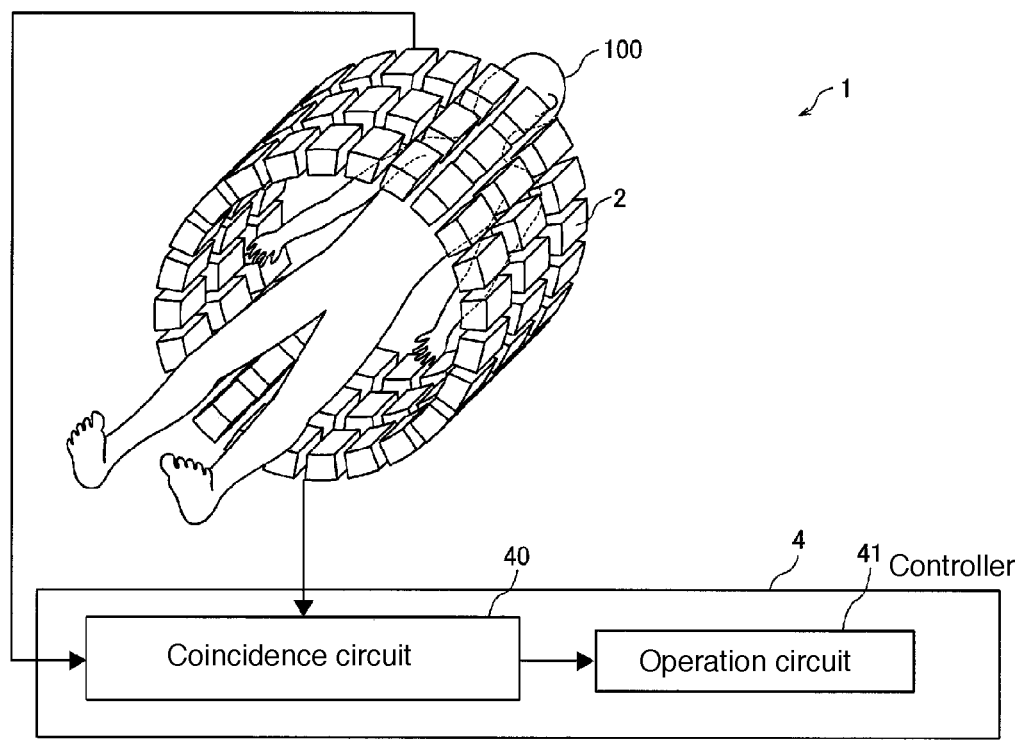
FIG. 1 is a schematic diagram showing a configuration of a PET device according to a first embodiment.

As shown in FIG. 1, the PET device 1 is a device for imaging a subject 100 by detecting radiation (γ rays) generated in the subject 100 due to a radiopharmaceutical agent that has been administered to the subject 100 in advance. Radiation (γ rays) is annihilation radiation generated in the subject 100 due to pair annihilation between a positron generated from a radiopharmaceutical agent and an electron of an atom in the vicinity of the positron. The PET device 1 is configured to generate the radioactivity distribution image of the subject 100 based on the imaging result of the subject 100. Note that the PET device 1 may be configured to be capable of imaging the whole body of the subject 100 or may be configured to be capable of imaging a part (such as, e.g., a breast and a head) of the subject 100. The PET device 1 is an example of the "nuclear medicine diagnostic apparatus" recited in claims.

The PET device 1 is provided with a detector ring 2 surrounding the subject 100. The detector ring 2 is provided in such a manner that a plurality of layers is laminated in the body axis direction of the subject 100. Inside the detector ring 2, a plurality of radiation (γ rays) detectors 3 (see FIG. 2) is provided. With this configuration, the detector ring 2 is configured to detect radiation (γ rays) generated from a radiopharmaceutical agent that has been administered to the subject 100. Note that the detector ring 2 is an example of the "detection unit" recited in claims.

Further, the PET device 1 is provided with a controller 4. The controller 4 includes a coincidence circuit 40 and an operation circuit 41. Note that in FIG. 1, although it is illustrated such that the radiation detector 3 (see FIG. 2) and the controller 4 (coincidence circuit 40) are connected by only two wiring. However, it is practically connected to the controller 4 (the coincidence circuit 40) by the total number of channels of the photomultiplier tube (PMT) 33 (see FIG. 2) of the radiation detector 3, which will be described later. Note that the operation circuit 41 is an example of the "operation unit" recited in claims. In some cases, a sensor other than a PMT, such as, e.g., a SiPM (Silicon Photomultiplier), may be used.

Figure 2:
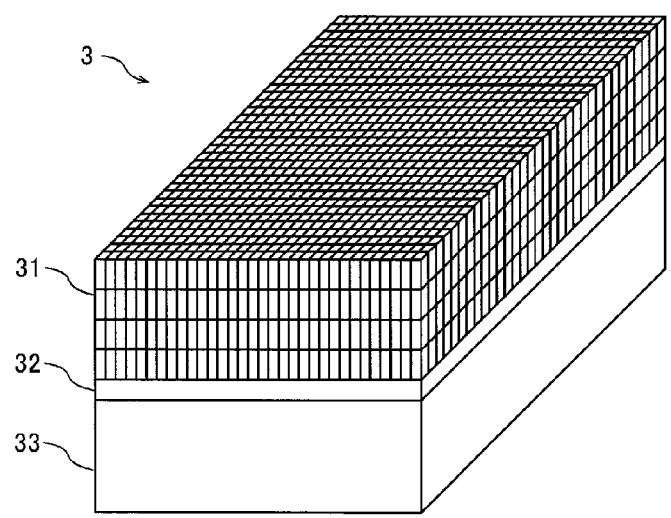
FIG. 2 is a schematic perspective view showing a configuration of a radiation (γ rays) detector according to the first embodiment.

As shown in FIG. 2, the radiation detector 3 includes a scintillator block 31, a light guide 32, and a photomultiplier tube 33. Note that in some cases, the light guide 32 is not used.

The scintillator block 31 converts the radiation (γ rays) generated from the subject 100 (see FIG. 1) to which a radiopharmaceutical agent has been administered into light. In a case where a radiopharmaceutical agent has been administered to the subject 100, two radiations (γ rays) are generated by the disappearance of the positron of a positron release type RI (Radio Isotope). Each scintillator element constituting the scintillator block 31 converts the radiation (γ rays) into light by emitting light in accordance with the incidence of the radiation (γ rays).

The light guide 32 is optically coupled to each of the scintillator block 31 and the photomultiplier tube 33. The light emitted in the scintillator element of the scintillator block 31 is diffused in the scintillator block 31 to be inputted to the photomultiplier tube 33 through the light guide 32.

The photomultiplier tube 33 multiplies the light inputted through the light guide 32 and converts it into an electric signal. This electric signal is transmitted to the coincidence circuit 40 (see FIG. 1).

The coincidence circuit 40 (see FIG. 1) generates detection signal data (count value) based on the electric signal transmitted from the photomultiplier tube 33.

Specifically, the coincidence circuit 40 (see FIG. 1) checks the position of the scintillator block 31 and the incident timing of the radiation (γ rays) and determines the electric signal transmitted only when radiation (γ rays) is simultaneously incident on the two scintillator blocks 31 on both sides of the subject 100 (on a diagonal line centered on the subject 100) as appropriate data. That is, the coincidence circuit 40 detects that the radiation (γ rays) is simultaneously observed (i.e., simultaneously counted) by the two radiation detectors 3 on both sides of the subject 100 (on the diagonal line centered on the subject 100) based on the electric signal described above.

The detection signal data (count value) configured by appropriate data which is determined to be coincidence by the coincidence circuit 40 is transmitted to the operation circuit 41 (see FIG. 1). The operation circuit 41 acquires list mode data as a detection result of the radiation (γ rays) by the detector ring 2. The list mode data means data in which the detection event information (the detector number, the detection time, the energy of radiation (γ rays), etc.) of the radiation (γ rays)) is stored in time series. The operation circuit 41 reconstructs the radioactivity distribution of the subject 100 from the list mode data by iterative calculation.

Configuration For Reconfiguring Radioactivity Distribution

Next, with reference to the flowchart of FIG. 3, the reconstruction processing of the radioactivity distribution of the subject 100 using the list mode data by the PET device 1 according to the first embodiment will be described. Note that each processing of the flowchart is performed by the operation circuit 41 of the controller 4.

Figure 3:
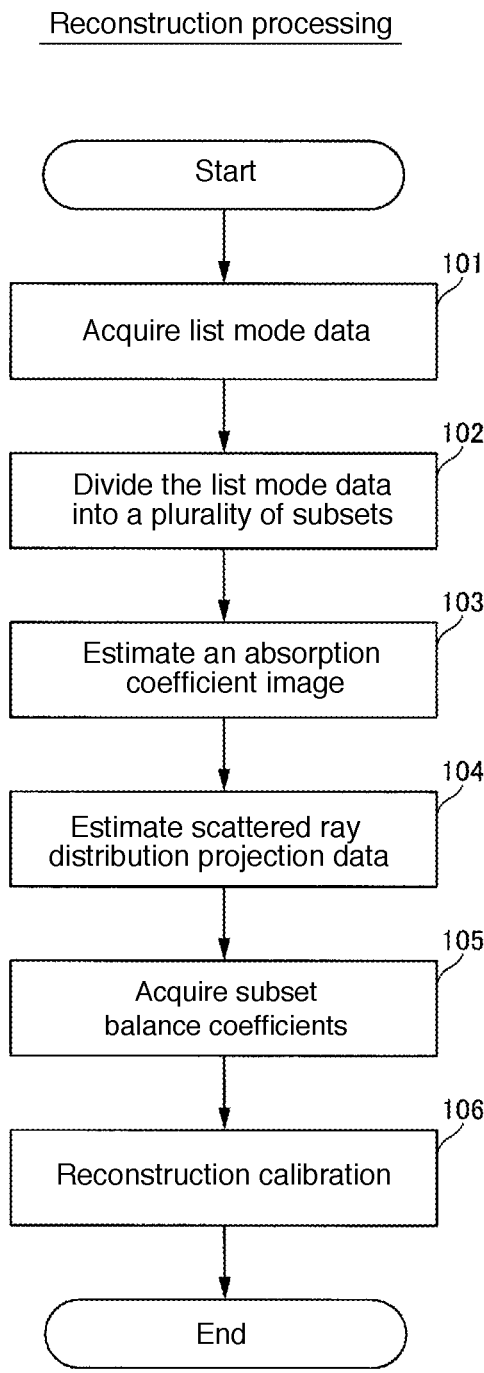
FIG. 3 is a flow diagram showing reconstruction processing according to the first embodiment.

First, as shown in FIG. 3, in Step 101, the PET device 1 images (measures) the subject 100 for a predetermined measurement time (e.g., 30 minutes) to acquire list mode data in a measurement time range. The list mode data in the measurement time range includes numerous events (actual measurement events).

Next, in Step 102, the list mode data in the measurement time range is divided into a plurality of subsets. Specifically, in Step 102, the list mode data is divided into a plurality of subsets by any one of an equal number of events division method, an equal number of ideal events division method, an equal event interval division method, and an equal time interval division method. Note that the subset division method and the number of subsets may be a specific method and a specific number predetermined in the PET device 1, or may be a method and the number specified by the user by inputting to the PET device 1.

The equal number of events division method is a subset division method in which actual measurement events in a reconstruction time range (i.e., a measurement time range) is divided into an equal (approximately equal) number of events. For example, it is supposed that list mode data with a total number of actual measurement events of 100,000 is divided into 10 subsets. In this case, in the equal number of events division method, the $1^{st}$ subset includes actual measurement events of the event numbers {1, 2, . . . , 10,000}, the $2^{nd}$ subset includes actual measurement events of the event numbers {10001, 10002, . . . , 20000}, and so on. As described above, the list mode data is equally divided from the first event by 10,000 events. Note that in a case where a fraction occurs, the fraction is included in the last subset ($10^{th}$ subset).

The equal number of ideal events division method is a subset division method in which actual measurement events in a reconstruction time range are divided into an equal (nearly equal) number of ideal events.

The number of ideal events denotes a number obtained by correcting the actual number of events by at least one factor selected from four physical factors consisting of physical attenuation of a radionuclide, counting loss of the detector 3, variation of the detection efficiency of the detector 3, and photon absorption by the subject 100. That is, the number of ideal events is an ideal number of ideal events when not affected by physical factors. Given a factor coefficient by at least one factor selected from four physical factors consisting of physical attenuation of a radionuclide, counting loss of the detector 3, variation of detection efficiency of the detector 3, photon absorption by the subject 100 as $\eta_t$, the number of ideal events of one actual measurement event can be represented by the inverse of $\eta_t$ (i.e., $1/\eta_t$). For this reason, the total number of ideal events can be represented by the following Formula (1):

$$X = \sum_{t=1}^{N} \frac{1}{\eta_t} \quad (1)$$

where
X: total number of ideal events
N: total number of actual measurement events
t: event number
$\eta_t$: factor coefficient Note that the factor used for the factor coefficient among the four physical factors may be an inherent one determined in advance in the PET device 1, or may be one specified by being inputted to the PET device 1 by the user.

The equal number of ideal events division method is a subset division method in which an actual measurement event in a reconstruction time range is divided such that the number of ideal events K of each subset becomes X/M, where the number of subsets is M. Specifically, in the equal number of ideal events division method, the number of ideal events (i.e., 1 per $\eta_j$) for each actual measurement event is accumulated. When the accumulated value of the number of ideal events at the actual measurement event of the event number $j_1$ exceeds K, the actual measurement events of the event numbers {1, 2, . . . , $j_1$} are set to a $1^{st}$ subset. When the accumulated value of the number of ideal events at the actual measurement event of the event number $J_2$ exceeds K, the actual measurement events of the event numbers {$j_1$+1, $j_2$+2, . . . , $j_2$} are set to $2^{nd}$ subset. As described above, the list mode data is divided equally so that the number of ideal events becomes K from the first event. Note that when a fraction occurs, the fraction is included in the last subset.

The equal event interval division method is a subset division method in which the actual measurement event in a reconstruction time range is divided at equal intervals of events. For example, it is supposed that the list mode data with a total number of actual measurement events of 100,000 is divided into 10 subsets. In this case, in the equal event interval division method, the $1^{st}$ subset includes the actual measurement events of the event numbers {1, 11, 21, . . . , 99991}, the $2^{nd}$ subset includes the actual measurement events of the event numbers {2, 12, 22, . . . , 99992}, and so on. Thus, the list mode data is divided from the first event every 10 events (events of the number of subsets).

The equal time interval division method is a subset division method in which an actual measurement event in a reconstruction time range is divided at equal time intervals. For example, it is supposed that list mode data with a reconstruction time range of 30 minutes is divided into 10 subsets. In this case, in the equal time interval division method, the list mode data is divided at time intervals, such that the $1^{st}$ subset includes the actual measurement events from 0 to 3 minutes in the reconstruction time range, the $2^{nd}$ subset includes the actual measurement events from 3 to 6 minutes in the reconstruction time range, etc.

Next, in Step 103, an absorption coefficient image for correcting absorption of radiation (γ rays) in the subject 100 is estimated. The estimation method of the absorption coefficient image is not particularly limited, but known methods, such as, e.g., a CT (Computed Tomography) image conversion method and a simultaneous estimation method, can be used. Further, as the simultaneous estimation method, for example, an MLAA (Maximum Likelihood Estimation of Attenuation and Activity) method, an MLACF (Maximum Likelihood Attenuation Correction Factors) method, or the like, can be used.

Next, in Step 104, scattered ray distribution projection data for correcting the scattering of the radiation (γ rays) within the subject 100 is estimated. The method of estimating the scattered ray distribution projection data is not particularly limited, but, for example, a known method, such as, e.g., a single scatter simulation method and a convolution method, can be used.

In the first embodiment, in Step 105, based on the number of events in a plurality of subsets, subset balance coefficients for adjusting the unevenness of the number of events between subsets are acquired. In Step 105, subset balance coefficients are acquired based on the ratio of the number of ideal events in the reconstruction time range to the number of ideal events in each subset. Specifically, the subset balance coefficient is acquired based on the ratio of the average number of ideal events in the reconstruction time range to the average number of ideal events in each subset. More specifically, the subset balance coefficient represented by the following Formulas (2) to (4) is acquired.

$$c_l = W/W_l \tag{2}$$

$$W_l = \frac{1}{|S_l|} \sum_{j \in S_l} \frac{1}{\eta_t} \tag{3}$$

$$W = \frac{1}{\sum_l |S_l|} \sum_l \sum_{j \in S_l} \frac{1}{\eta_t} \tag{4}$$

where
W: average number of ideal events in a reconstruction time range
$W_l$: average number of ideal events in the $1^{st}$ subset
l: subset number
$C_l$: subset balance coefficient
$S_l$: a set of actual measurement events belonging to the $1^{st}$ subset
t: event number in the l-th subset
j: pixel number
$\eta_t$: factor coefficient for the t-th event in the l-th subset For example, in a case where the list mode data is divided into 10 subsets, according to Formulas (2) to (4), 10 pieces of subset coefficients of $c_1$ to $c_{10}$ corresponding to the $1^{st}$ to $10^{th}$ subsets, respectively, are acquired. In other words, in Step 105, the subset balance coefficient for each subset is acquired. The subset balance coefficient is a positive coefficient that depends on the subset number. Note that the effects of the subset balance coefficient will be described in detail later.

Next, in Step 106, reconstruction calculation is performed in which the radioactivity distribution of the subject 100 is reconstructed by iterative calculation from the list mode data. Specifically, in Step 106, reconstruction calculation including a step of acquiring back projection values based on the list mode data, a step of acquiring corrected back projection values by multiplying the back projection values by subset balance coefficients, a step of acquiring a back projection image based on the corrected back projection values, and a step of updating a radioactivity distribution image based on the back projection image. More specifically, reconstruction calculation is performed by the following Formulas (5) to (8). Note that subset balance coefficients are introduced in Formula (5). Further, Formula (5) is a formula using a DRAMA (Dynamic Row-Action Maximum Likelihood Algorithm) method including back projection calculation as a list mode reconstruction algorithm.

$$x_j^{(k,l+1)} = x_j^{(k,l)} + \lambda^{(k,l)} \frac{x_j^{(k,l)}}{C_j} \sum_{t \in S_l} a_{i(t)j} \left( \frac{c_l \times \frac{1}{(T_{acq} \times h_t)}}{\sum_{j'=1}^{J} a_{i(t)j'} x_{j'}^{(k,l)} + r_{i(t)}} - p_j \right) (l = 0, \ldots, L-1) \tag{5}$$

$$x_j^{(k+1,0)} = x_j^{(k,L)}$$

$$p_j = \sum_{i=1}^{I} a_{ij} / \sum_{l=0}^{L-1} \sum_{t \in S_l} a_{i(t)j} \tag{6}$$

$$C_j = \max_l \sum_{t \in S_l} a_{i(t)j} p_{lj} \tag{7}$$

$$\lambda^{(k,l)} = \beta_0 / (\beta_0 + l + \gamma k L) \tag{8}$$

where
k: number of iterations
l: subset number
L: number of subsets
$S_l$: a set of actual measurement events belonging to the $1^{st}$ subset
t: event number
i: detector number
j: pixel number
$x_j$: $j^{th}$ pixel value of a radioactivity distribution image to be estimated
$a_{ij}$: probability (value independent of time) that radiation occurred in the $j^{th}$ pixel is detected by the $i^{th}$ detector
$r_i$: average coefficient rate of a background event
$T_{acq}$: measurement time (sec)
$h_t$: product of a physical attenuation coefficient at the detection time of the $t^{th}$ actual measurement event and a counting loss coefficient for the $t^{th}$ actual measurement event $\beta_0$, γ: relaxation parameter In Formula (5), the back projection value is a portion represented by the following Expression (9), the corrected back projection value is a portion represented by the following Expression (10), and the back projection image is a portion represented by the following Expression (11).

$$\frac{1}{(T_{acq} \times h_t)} \tag{9}$$

$$c_l \times \frac{1}{(T_{acq} \times h_t)} \tag{10}$$

$$\sum_{t \in S_l} a_{i(t)j} \left( \frac{c_l \times \frac{1}{(T_{acq} \times h_t)}}{\sum_{j'=1}^{J} a_{i(t)j'} x_{j'}^{(k,l)} + r_{i(t)}} - p_j \right) \tag{11}$$

As shown in Formula (5), the reconstruction calculation includes a first step of updating a radioactivity distribution image for each subset, and a second step of repeating the first step by the number of iterations (i.e., by k times). In the first step, a step of acquiring back projection values based on the above-described list mode data, a step of acquiring corrected back projection values by multiplying the back projection values by the subset balance coefficients, a step of acquiring a back projection image based on the corrected projection values, and a step of updating the radioactivity distribution image based on the back projection image, are performed for each subset.

For example, in a case where the list mode data is divided into 10 subsets, in the first step, a radioactivity distribution image is updated by sequentially performing calculation from the $1^{st}$ subset to the $10^{th}$ subset such that a radioactivity distribution image is updated by the $1^{st}$ subset using the subset balance coefficient $c_1$ corresponding to the $1^{st}$ subset, a radioactivity distribution image (radioactivity distribution image updated by the $1^{st}$ subset) is updated by the $2^{nd}$ subset using a subset balance coefficient $c_2$ corresponding to the $2^{nd}$ subset, and so on. In the second step, the calculation of the first step is repeated by the number of iterations.

Upon completion of the reconstruction calculation including the first step and the second step, a quantitative radioactivity distribution image is acquired in which the pixel value of each pixel converges to a value indicating the radioactive concentration of the subject 100.

Description of Effects of Subset Balance Coefficient

Next, with reference to FIGS. 4 to 7, the effects of the subset balance coefficient will be described.

Figure 4:
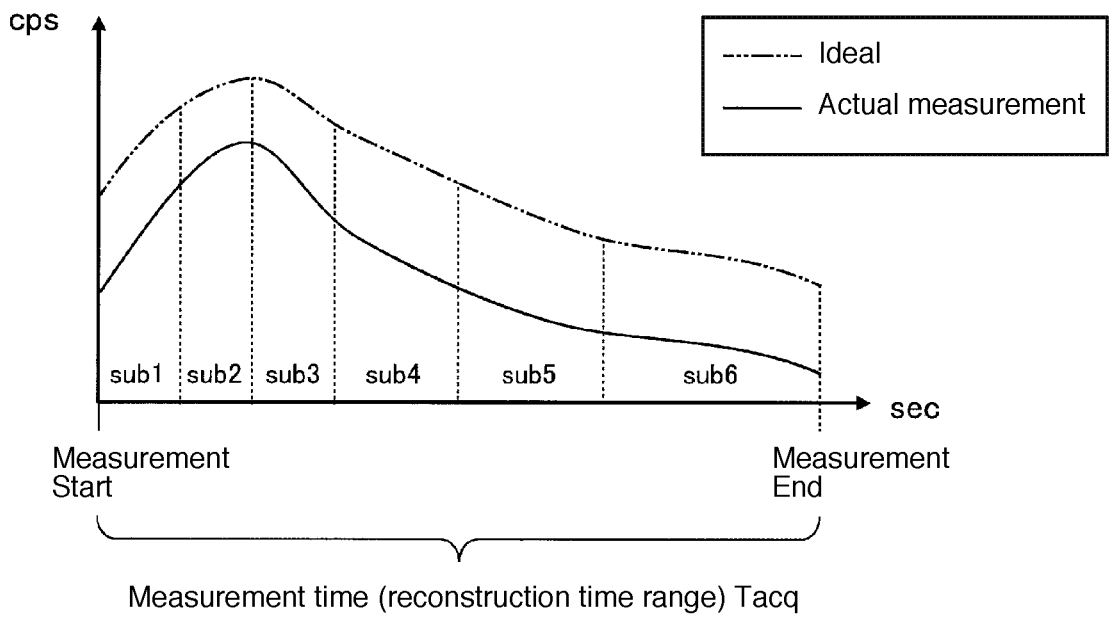
FIG. 4 is a diagram for explaining the effects of subset balance coefficients according to the first embodiment and is a schematic graph showing a change in a count rate with respect to a measurement time.

FIG. 4 is a schematic graph showing the change in the count rate with respect to the measurement time when imaging the subject 100. In FIG. 4, the vertical axis represents the count rate (cps: count/sec), and the horizontal axis represents time (sec). In the graph of FIG. 4, the time change of the actual measurement count rate is shown by a solid line, and the time change of the ideal count rate is shown by a two-dot chain line. As described above, note that the time change of the ideal count rate change is acquired by multiplying the inverse of the factor coefficient $\eta_t$ (i.e., $1/\eta_t$) by the time change of the actual measurement count rate. That is, the time change of the ideal count rate is a time change of the ideal count rate in a case where there is no effect of physical factors.

The graph of FIG. 4 shows that the list mode data is divided into six subsets by an equal number of events division method. In the graph of FIG. 4, the six subsets are illustrated as sub1, sub2, sub3, sub4, sub5, and sub6. In the example of FIG. 4, the number of the actual measurement events is equal (nearly equal) in the six subsets of sub1 to sub6 because they are divided by an equal number of events division method. On the other hand, in the 6 subsets of sub1 to sub6, the time width of each subset is uneven, and the number of ideal events in each subset is uneven.

Figure 5:
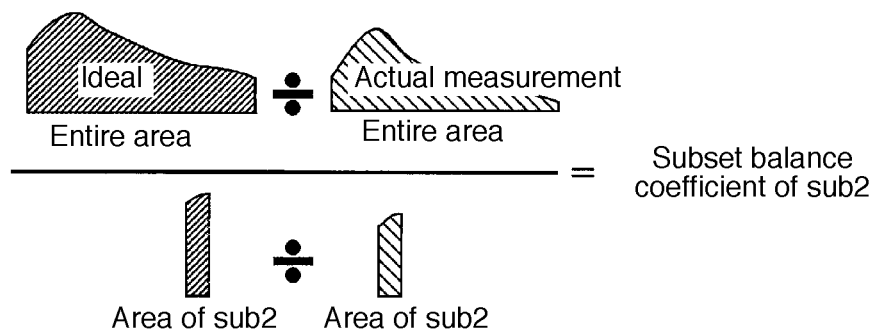
FIG. 5 is a diagram for explaining the effects of subset balance coefficients according to the first embodiment and is a schematic diagram for explaining a concept of the subset balance coefficient.

FIG. 5 is a schematic diagram for explaining the concept of the subset balance coefficient.

As shown in FIG. 5, the average number of ideal events in the reconstruction time range, which is a numerator of a subset balance coefficient represented by (average number of ideal events in the reconstruction time range)/(average number of ideal events in subsets), can be expressed as a number obtained by dividing the area of the time change of the entire number of ideal count rates 3 in the entire reconstruction time range by the area of the time change of the actual measurement count rate in the entire reconstruction time range. Further, the average number of ideal events in a subset (sub2), which is a denominator of a subset balance coefficient, can be represented by a number obtained by dividing the area of the time change of the ideal count rate of the subset (sub2) in the reconstruction time range by the area of the time change of the actual measurement count rate of the subset (sub2) in the reconstruction time range. Note that since the area is determined by cps×sec, the unit of each area is "count."

In FIG. 5, although an example is shown in which a subset balance coefficient of the sub2 is acquired, subset balance coefficients can be acquired by the same calculation for subsets other than the sub2, i.e., the sub1, and the sub3 to the sub6.

Figure 6:
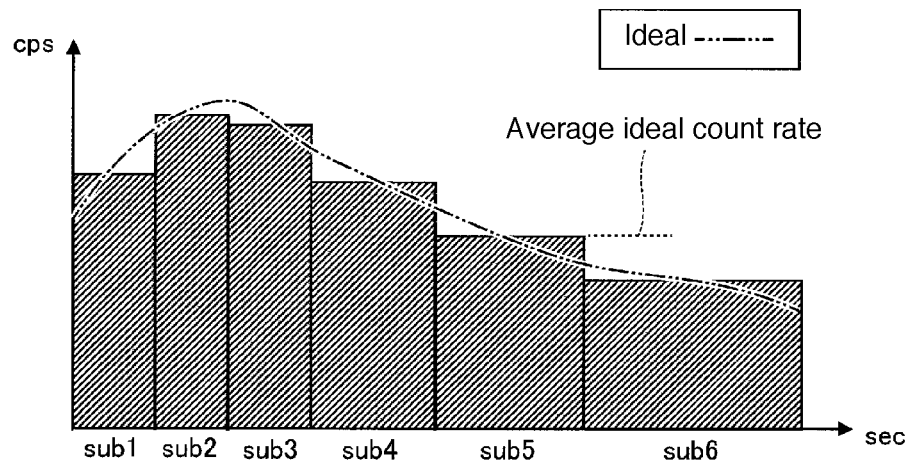
FIG. 6 is a diagram for explaining the effects of subset balance coefficients according to the first embodiment and is a schematic diagram showing a state of an area of each subset before correcting subset balance coefficients.

FIG. 6 is a schematic diagram showing the state of the area of each subset (the sub1 to the sub6) before correcting (before multiplying) the subset balance coefficient. In FIG. 6, the area of the time change of the ideal count rate of each subset is represented by a rectangular shape using the average ideal count rate of each subset. Note that the average ideal count rate of each subset means the mean value of the ideal count rates in the time range of each subset. In FIG. 6, the area of the time change of the ideal count rate of each subset is represented by a rectangular shape in which the average ideal count rate of each subset is the upper end value. Note that in FIG. 6, although only the average ideal count rate of the sub5 is shown, the upper end values of the rectangular shapes for subsets other than the sub5, i.e., the sub1 to the sub4 and the sub6, are also average ideal count rates. In FIG. 6, the areas of the subsets are uneven in the sub1 to the sub6. That is, in the sub1 to the sub6, the number of ideal events in each subset is uneven. In this case, since the number of ideal events in each subset is uneven and not uniform, the quantitative radioactive concentration cannot be acquired.

Figure 7:
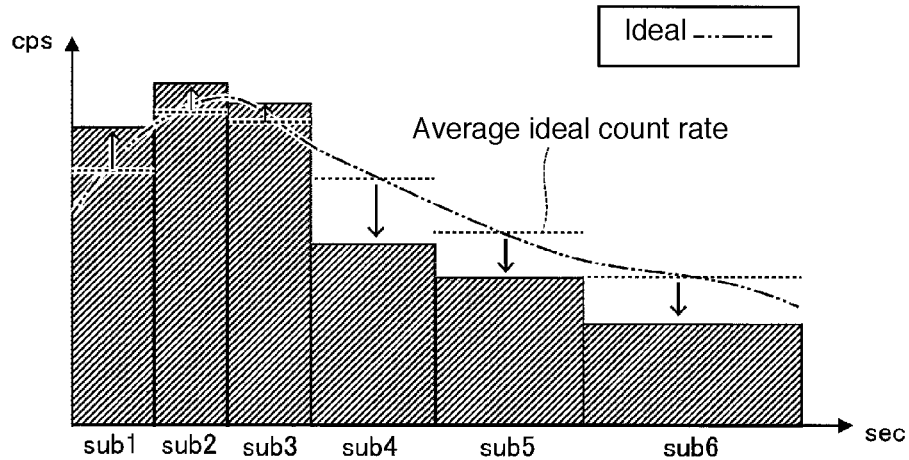
FIG. 7 is a schematic diagram for explaining the effects of subset balance coefficients according to the first embodiment and is a schematic diagram showing a state of an area of each subset after correcting subset balance coefficients.

FIG. 7 is a schematic diagram showing the state of the area of each subset after correcting (after multiplying) the subset balance coefficient. In FIG. 7, to facilitate the understanding, the position of the average ideal count rate of each subset before correcting the subset balance coefficient (i.e., the upper end position of the rectangular shape representing the area of each subset in FIG. 6) is shown by a broken line. In FIG. 7, by multiplying the area of the subset by the subset balance coefficient, the areas of the sub1 to the sub3, which were relatively small, become larger, while the areas of the sub4 to the sub6, which were relatively large, become smaller.

Multiplying the subset balance coefficient means, as described above, dividing the area of the subset by the "average number of ideal events in subsets" and then multiplying the "average number of ideal events in the reconstruction time range" independent of a subset. Therefore, by multiplying the area of each subset by the subset balance coefficient, the area of each subset is aligned (becomes nearly equal). That is, by multiplying the area of each subset by the subset balance coefficient, the number of ideal events in each subset is aligned (becomes nearly equal), and therefore, a quantitative radioactive concentration can be obtained.

Actual Image

Figure 8:
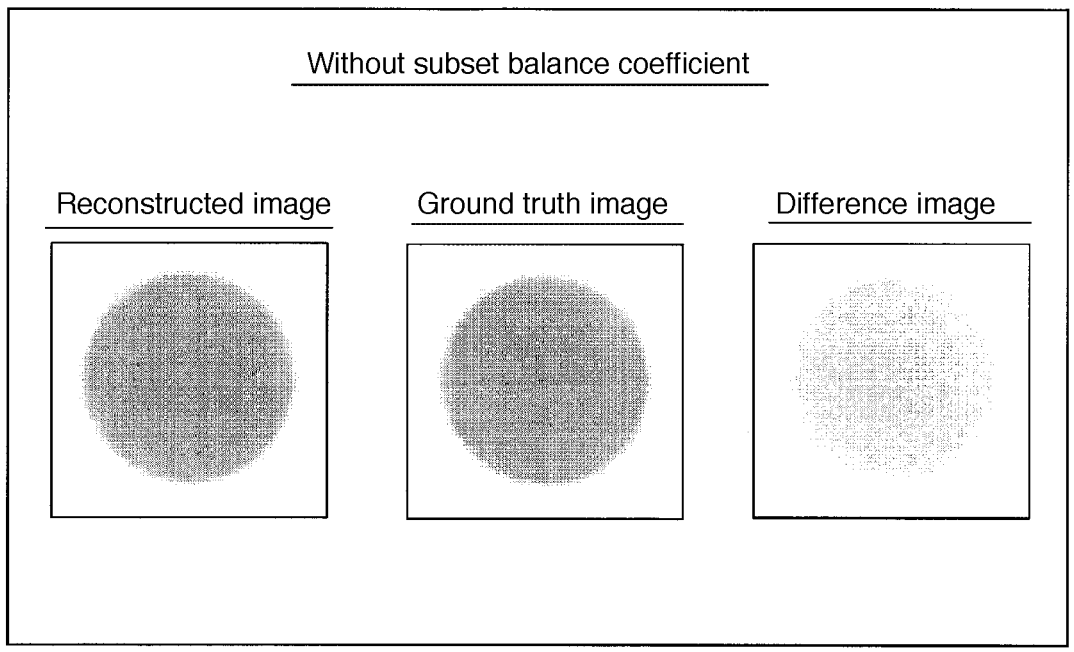
FIG. 8 is a diagram showing an example of an actual reconstructed image reconfigured without using subset balance coefficients, an example of a ground truth image, and a difference image between the reconstructed image and the ground truth image.
Figure 9:
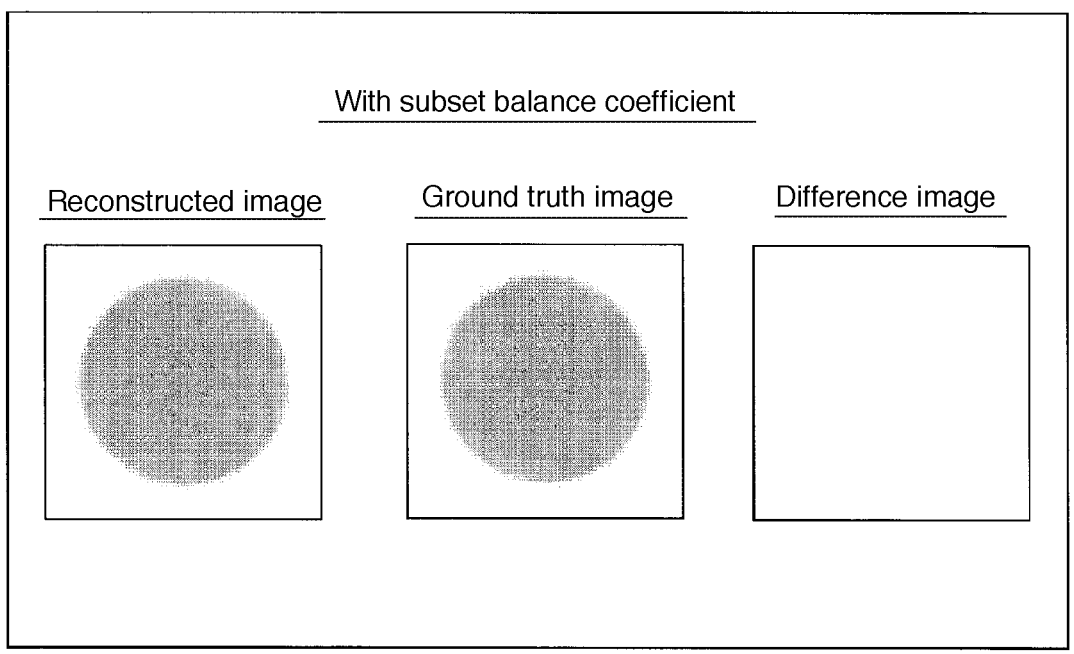
FIG. 9 is a diagram showing an example of an actual reconstructed image reconstructed using subset balance coefficients, an example of a ground truth image, and a difference image between the reconstructed image and the ground truth image.

Next, with reference to FIGS. 8 and 9, an actual reconstructed image (radioactivity distribution image) will be described. FIG. 8 is a diagram showing an example of an actual reconstructed image reconfigured without using subset balance coefficients, an example of a ground truth image, and a difference image between the reconstructed image and the ground truth image. FIG. 9 is a diagram showing an example of an actual reconstructed image reconfigured using subset balance coefficients, an example of a ground truth image, and a difference image between the reconstructed image and the ground truth image.

In both the cases of FIGS. 8 and 9, the subset division method is an equal number of events division method, and the number of subsets is 100. For the reconstruction calculation of the reconstructed image of FIG. 8, the above-described Formula (5) not including subset balance coefficients are used, and for the reconstruction calculation of the reconstructed image of FIG. 9, the above-described Formula (5) including subset balance coefficients are used. Further, in both the cases of FIG. 8 and FIG. 9, as the ground truth image, a reconstructed image in which the number of subsets is 1 is used.

As shown in FIG. 8, in the case of not using subset balance coefficients, the difference image between the reconstructed image and the ground truth image has not become zero. That is, in the reconstructed image, the calculated value (pixel value) of iterative calculation has not converged to the value (the value of the ground truth image) indicating the radioactive concentration of the subject 100. Therefore, in the case of not using the subset balance coefficient, the quantitative reconstructed image (radioactivity distribution image) cannot be obtained.

On the other hand, as shown in FIG. 9, in the case of using subset balance coefficients, the difference image between the reconstructed image and the ground truth image has become zero. That is, in the reconstructed image, the calculated value (pixel value) of iterative calculation has converged to the value (the value of the ground truth image) indicating the radioactive concentration of the subject 100. Therefore, by using the subset balance coefficient, a quantitative reconstructed image (radioactivity distribution image) can be obtained. Not that similar results can be obtained even in a case where the number of subsets is changed.

Effects of First Embodiment

In the first embodiment, the following effects can be obtained.

In the first embodiment, as described above, the list mode data is divided into a plurality of subsets, subset balance coefficient are acquired based on the number of events in the plurality of subsets, back projection values are acquired based on the list mode data, modified back projection values are acquired by multiplying the back projection value by the subset balance coefficients, a back projection image is acquired based on the corrected back projection values, and a radioactivity distribution image is updated based on the back projection image. This makes it possible to adjust the unevenness of the number of events between subsets by introducing the subset balance coefficient, and therefore, it is possible to suppress the situation in which the calculated value (pixel value) of iterative calculation does not converge to the value indicating the radioactive concentration of the subject due to the unevenness of the number of events between subsets. In other words, since it is possible to make the calculated value of iterative calculation converge to a value indicating the radioactive concentration of the subject, a quantitative radioactivity distribution image can be generated. In addition, by introducing the subset balance coefficient, even in a case where the number of subsets is changed, the unevenness of the number of events between subsets can be adjusted, and therefore, it is possible to suppress the pixel value from changing depending on the number of subsets. That is, an equivalent pixel value can be obtained without relying on the number of subsets. As a result, a quantitative radioactivity distribution image can be generated without relying on the number of subsets.

In the first embodiment, as described above, the subset balance coefficient is acquired based on the ratio of the number of ideal events in the reconstruction time range to the number of ideal events in each subset. With this, the unevenness of the number of ideal events between subsets can be easily adjusted based on the ratio of the number of ideal events in the reconstruction time range to the number of ideal events in each subset. Therefore, it is possible to easily make the calculated value of iterative calculation converge to the value indicating the radioactive concentration of the subject.

Further, in the first embodiment, as described above, the subset balance coefficient is acquired based on the ratio of the average number of ideal events in the reconstruction time range to the average number of ideal events in each subset. With this, it is possible to easily adjust the unevenness of the number of ideal events between subsets based on the ratio of the number of ideal events in the reconstruction time range to the number of ideal events in each subset. Therefore, it is possible to easily make the calculated value of iterative calculation converge to the value indicating the radioactive concentration of the subject. Note that this configuration is particularly useful when a subset is divided by an equal number of events division method.

Further, in the first embodiment, as described above, the number of ideal events is a number obtained by correcting the number of actual measurement events by at least one factor selected from four physical factors consisting of physical attenuation of a radionuclide, counting loss of a detector, variation of detection efficiency of a detector, and photon absorption of a subject. With this, the actual measurement number of events can be corrected by at least one factor selected from four physical factors consisting of physical attenuation of a radionuclide, counting loss of a detector, variation of detection efficiency of a detector, and photon absorption by a subject. Thus, the number of ideal events can be accurately acquired.

Further, in the first embodiment, as described above, the subset balance coefficient for each subset is acquired. This makes it possible to adjust the unevenness of the number of ideal events between subsets with subset balance coefficients suitable for each subset, which makes it possible to assuredly adjust the unevenness of the number of ideal events between subsets.

Further, in the first embodiment, as described above, the list mode data is divided into a plurality of subsets by any one of an equal number of events division method, an equal number of ideal events division method, an equal event interval division method, and an equal time interval division method. This allows the list mode data to be easily divided into a plurality of subsets by any one of an equal number of events division method, an equal number of ideal events division method, an equal event interval division method, and an equal time interval division method.

Second Embodiment

Next, with reference to FIG. 10, a second embodiment of the present invention will be described. In the second embodiment, an example in which subset balance coefficients different from the first embodiment is used will be described. Note that the same reference numeral is allotted to the same configuration as that of the first embodiment in the drawings, and the description thereof will be omitted.

Configuration of PET Device

Figure 10:
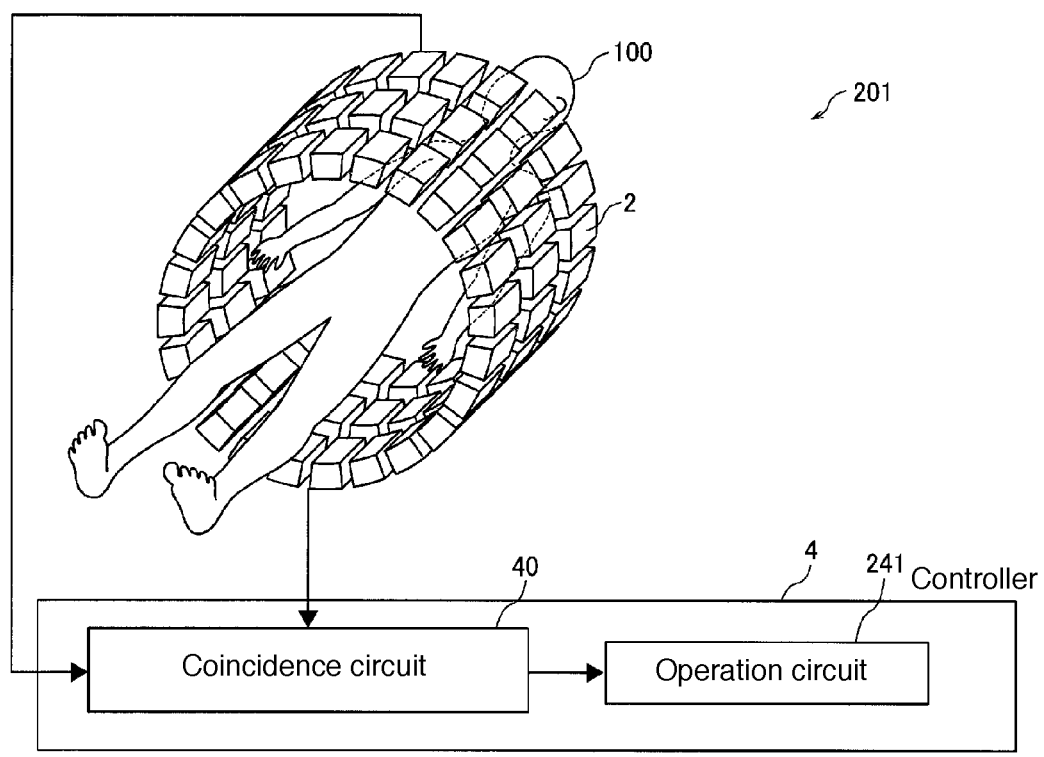
FIG. 10 is a schematic diagram showing a configuration of a PET device according to a second embodiment.

In the second embodiment, as shown in FIG. 10, a PET device 201 is provided with an operation circuit 241 instead of the operation circuit 41 of the first embodiment. Note that the PET device 201 is an example of the "nuclear medicine diagnostic apparatus" recited in claims. Further note that the operation circuit 241 is an example of the "operation unit" recited in claims.

The operation circuit 241 is configured to acquire subset balance coefficients based on a ratio of the number of ideal events in a reconstruction time range to a value obtained by multiplying the number of ideal events inf each subset by the number of subsets. Specifically, the operation circuit 241 is configured to acquire subset balance coefficients represented by the following Formulas (12) to (14).

$$c_l = W/W_l \quad (12)$$

$$W_l = \sum_{j \in S_l} \frac{1}{\eta_t} \times L \quad (13)$$

$$W = \sum_l \sum_{j \in S_l} \frac{1}{\eta_t} \quad (14)$$

where

L: number of subsets

W: number of ideal events in a reconstruction time range (the total number of ideal events)

$W_1$: number obtained by multiplying the number of ideal events in the $1^{st}$ subset by the number of subsets l: subset number $C_1$: subset balance coefficient $S_1$: a set of actual measurement events belonging to the $1^{st}$ subset t: event index in 1th subset j: pixel number $\eta_t$: factor coefficient for the t-th event in the 1th subset In the second embodiment, the operation circuit 241 is configured to perform reconstruction calculation by a formula in which the subset balance coefficient of Formula (12) is introduced into Formula (5) of the first embodiment, instead of the subset balance coefficient of Formula (2) of the first embodiment. Note that the details of the reconstruction calculation are the same as those of the above-described first embodiment, and therefore the detailed descriptions thereof are omitted.

Further, the rest of the configuration of the second embodiment is the same as that of the first embodiment.

Effects of Second Embodiment

In the second embodiment, the following effects can be obtained.

In the second embodiment, as described above, the subset balance coefficient is acquired based on the ratio of the number of ideal events in the reconstruction time range to a value obtained by multiplying the number of ideal events in each subset by the number of subsets. This makes it possible to acquire subset balance coefficients that are more versatile than when acquiring subset balance coefficients (in the case of the first embodiment), based on the ratio of the number of ideal events in the reconstruction time range to the number of ideal events in a subset. Therefore, the unevenness of the number of ideal events between subsets can be adjusted more easily.

Note that other effects of the second embodiment are the same as those of the first embodiment.

Modifications

It should be understood that the embodiments disclosed here are examples in all respects and are not restrictive. The scope of the present invention is shown by the claims rather than the descriptions of the embodiments described above, and includes all changes (modifications) within the range and the meaning equivalent to the claims.

For example, in the above-described first and second embodiments, an example is shown in which a nuclear medicine diagnostic apparatus is a PET device, but the present invention is not limited thereto. For example, the nuclear medicine diagnostic apparatus may be a SPECT (Single photon emission computed tomography) device other than a PET device.

In addition, in the above-described first and second embodiments, an example is shown in which subset balance coefficients represented by Formulas (2) to (4) or Formulas (12) to (14) is acquired, but the present invention is not limited thereto. In the present invention, subset balance coefficients other than the subset balance coefficient represented by Formulas (2) to (4) or Formula (12) to (14) may be acquired as long as the unevenness of the number of events between subsets can be adjusted.

Further, in the above-described first and second embodiments examples, an example is shown in which subset balance coefficients are introduced into Formula (5) using a DRAMA method including a back projection calculation as a list mode reconstruction algorithm, but the present invention is not limited thereto. In the present invention, subset balance coefficients may be introduced into a formula using an OSEM (Ordered Subsets Expectation Maximization) method other than a DRAMA method including back projection processing as a list mode reconstruction algorithm. That is, in the present invention, the introduction of the subset balance coefficient is not limited to an application to any particular list mode reconstruction algorithm.

Further, in the above-described first and second embodiments, an example is shown in which a radioactivity distribution of a subject is reconfigured from the list mode data after completion of imaging the subject, but the present invention is not limited thereto. In the present invention, the radioactivity distribution of the subject may be reconfigured in real-time when a subject is being imaged from list mode data during imaging the subject. For example, it may be configured such that the list mode data when the imaging of the subject is completed is estimated from the list mode data (list mode data in progress) when the subject is being imaged and that the radioactivity distribution of the subject is reconstructed from the estimated list mode data. In this case, the estimated list mode data may be divided into a plurality of subsets in the same manner as in the first or second embodiment, and subset balance coefficients may be acquired in the same manner as in the first or second embodiment. Alternatively, for example, a radioactivity distribution of a subject may be directly reconstructed from list mode data (list mode data in progress) during imaging the subject. In this instance, the list mode data (list mode data in progress) during imaging the subject may be divided into a plurality of subsets in the same manner as in the first or second embodiment, and subset balance coefficients may be acquired in the same manner as in the first or second embodiment.

Further, in the first and second embodiments, for convenience of explanation, each processing of the operation circuit 41 (241) is described using a "flow-driven" flowchart, but the present invention is not limited thereto. In the present invention, the above-described each processing may be performed by an "event-driven type" which is executed on an event-by-event basis. In this case, the processing may be performed by a complete event-driven type processing or by a combination of event-driven type processing and flow-driven type processing.

Further, in the first and second embodiments, an example is shown in which back projection values are multiplied by subset balance coefficients, but the present invention is not limited thereto. In the present invention, a back projection image may be multiplied by subset balance coefficients. That is, since the subset balance coefficient is independent of the event number in a subset, Expression (11) representing a back projection image can be represented by the following Expression (15).

$$c_l \times \sum_{t \in S_l} a_{i(t)j} \left( \frac{\frac{1}{(T_{acq} \times h_t)}}{\sum_{j'=1}^{J} a_{i(t)j'} x_{j'}^{(k,l)} + r_{i(t)}} - p_j \right) \quad (15)$$

Aspects

It will be understood by those skilled in the art that the above-described exemplary embodiments are concrete examples of the following aspects.

Item 1

A list mode image reconstruction method for reconstructing a radioactivity distribution of a subject from list mode data collected by a nuclear medicine diagnostic apparatus by iterative calculation, the list mode image reconstruction method comprising the steps of:
dividing the list mode data into a plurality of subsets;
acquiring subset balance coefficients based on the number of events in the plurality of subsets;
acquiring back projection values based on the list mode data;
acquiring a back projection image based on the back projection value;
multiplying the back projection value or the back projection image by the subset balance coefficient; and
updating a radioactivity distribution image based on the back projection image.

Item 2

The list mode image reconstruction method as recited in the above-described Item 1,
wherein the step of acquiring the subset balance coefficient includes a step of acquiring the subset balance coefficient based on a ratio of the number of ideal events in a reconstruction time range to the number of ideal events in each subset.

Item 3

The list mode image reconstruction method as recited in the above-described Item 2,
wherein the step of acquiring the subset balance coefficient includes a step of acquiring the subset balance coefficient based on a ratio of an average number of ideal events in a reconstruction time range to the number of ideal events in each subset.

Item 4

The list mode image reconstruction method as recited in the above-described Item 2,
wherein the step of acquiring the subset balance coefficient includes a step of acquiring the subset balance coefficient based on a ratio of the number of ideal events in the reconstruction time range to a value acquired by multiplying the number of ideal events in each subset by the number of subsets.

Item 5

The list mode image reconstruction method as recited in any one of the above-described Items 2 to 4,
wherein the number of ideal events is a number acquired by correcting the number of actual measurement events by at least one factor selected from four physical factors consisting of physical attenuation of a radionuclide, counting loss of a detector, variation of detection efficiency of a detector, and photon absorption by the subject.

Item 6

The list mode image reconstruction method as recited in any one of the above-described Items 1 to 5,
wherein the step of acquiring the subset balance coefficient includes a step of acquiring the subset balance coefficient for each subset.

Item 7

The list mode image reconstruction method as recited in any one of the above-described Items 1 to 6,
wherein the step of dividing the list mode data into the plurality of subsets includes a step of dividing the list mode data into the plurality of subsets by any one of an equal number of events division method, an equal number of ideal events division method, an equal event interval division method, and an equal time interval division method.

Item 8

A nuclear medicine diagnostic apparatus comprising:
a detection unit configured to detect radiation generated from a radiopharmaceutical agent in a subject; and
an operation unit configured to reconstruct a radioactivity distribution of the subject from list data as a detection result of radiation by the detection unit by iterative calculation,
wherein the operation unit
divides the list mode data into a plurality of subsets,
acquires subset balance coefficients based on the number of events in the plurality of subsets,
acquires back projection values based on the list mode data,
acquires a back projection image based on the back projection value,
multiplies the back projection value or the back projection image by the subset balance coefficient, and
updates a radioactivity distribution image based on the back projection image.

Item 9

The nuclear medicine diagnostic apparatus as recited in the above-described Item 8,
wherein the operation unit is configured to acquire the subset balance coefficient based on a ratio of the number of ideal events in a reconstruction time range to the number of ideal events in each subset.

Item 10

The nuclear medicine diagnostic apparatus as recited in the above-described Item 9,
wherein the operation unit is configured to acquire the subset balance coefficient based on a ratio of the average number of ideal events in a reconstruction time range to an average number of ideal events in each subset.

Item 11

The nuclear medicine diagnostic apparatus as recited in the above-described Item 9,
wherein the operation unit is configured to acquire the subset balance coefficient based on a ratio of the number of ideal events in a reconstruction time range to a value obtained by multiplying the number of ideal events in each subset by the number of subsets.

DESCRIPTION OF SYMBOLS 1, 201: PET device (nuclear medicine diagnostic apparatus)
2: Detector ring (detection unit)
41, 241: Operation circuit (operation unit)
100: T: subject

The invention claimed is:

1. A list mode image reconstruction method for reconstructing a radioactivity distribution image of a subject from list mode data collected by a nuclear medicine diagnostic apparatus by iterative calculation, the list mode image reconstruction method comprising the steps of:
dividing the list mode data into a plurality of subsets;
acquiring subset balance coefficients for adjusting the number of events in the plurality of subsets based on the number of events in the plurality of subsets;
acquiring back projection values based on the list mode data;
acquiring corrected back projection values by multiplying the back projection values by the subset balance coefficients;
acquiring a back projection image based on the corrected back projection values, and
updating the radioactivity distribution image based on the back projection image.

2. The list mode image reconstruction method as recited in claim 1,
wherein the step of acquiring the subset balance coefficients includes a step of acquiring the subset balance coefficients based on a ratio of the number of ideal events in a reconstruction time range to the number of ideal events in each subset.

3. The list mode image reconstruction method as recited in claim 2,
wherein the step of acquiring the subset balance coefficients includes a step of acquiring the subset balance coefficient based on a ratio of an average number of ideal events in the reconstruction time range to the number of ideal events in each subset.

4. The list mode image reconstruction method as recited in claim 2,
wherein the step of acquiring the subset balance coefficients includes a step of acquiring the subset balance coefficients based on a ratio of the number of ideal events in the reconstruction time range to a value acquired by multiplying the number of ideal events in each subset by the number of subsets.

5. The list mode image reconstruction method as recited in claim 2,
wherein the number of ideal events is a number acquired by correcting the number of measured events by at least one factor selected from four physical factors consisting of radioactive decay, counting loss of a detector, variation of detection efficiency of a detector, and photon attenuation by the subject.

6. The list mode image reconstruction method as recited in claim 1,
wherein the step of acquiring the subset balance coefficients includes a step of acquiring the subset balance coefficient for each subset.

7. The list mode image reconstruction method as recited in claim 1,
wherein the step of dividing the list mode data into the plurality of subsets includes a step of dividing the list mode data into the plurality of subsets by any one of an equal number of events division method, an equal number of ideal events division method, an equal event interval division method, and an equal time interval division method.

8. A nuclear medicine diagnostic apparatus comprising:
a detection unit configured to detect radiation generated from a radiopharmaceutical agent in a subject; and
an operation unit configured to reconstruct a radioactivity distribution image of the subject from list mode data as a detection result of radiation by the detection unit by iterative calculation,
wherein the operation unit
divides the list mode data into a plurality of subsets,
acquires subset balance coefficients for adjusting the number of events in the plurality of subsets based on the number of events in the plurality of subsets,
acquires back projection values based on the list mode data,
acquires a corrected back projection value by multiplying the back projection values by the subset balance coefficients, and
acquires a back projection image based on the corrected back projection values, and
updates the radioactivity distribution image based on the back projection image.

9. The nuclear medicine diagnostic apparatus as recited in claim 8,
wherein the operation unit is configured to acquire the subset balance coefficients based on a ratio of the number of ideal events in a reconstruction time range to the number of ideal events in each subset.

10. The nuclear medicine diagnostic apparatus as recited in claim 9,
wherein the operation unit is configured to acquire the subset balance coefficients based on a ratio of the average number of ideal events in the reconstruction time range to an average number of ideal events in each subset.

11. The nuclear medicine diagnostic apparatus as recited in claim 9,
wherein the operation unit is configured to acquire the subset balance coefficients based on a ratio of the number of ideal events in the reconstruction time range to a value obtained by multiplying the number of ideal events in each subset by the number of subsets.

* * * * *